(12) United States Patent
Bürgi et al.

(10) Patent No.: US 10,241,107 B2
(45) Date of Patent: Mar. 26, 2019

(54) CONCENTRATION MEASUREMENTS WITH A MOBILE DEVICE

(71) Applicant: Sensirion AG, Stäfa (CH)

(72) Inventors: Lukas Bürgi, Zürich (CH); Felix Mayer, Stäfa (CH); Samuel Wehrli, Wädenswil (CH)

(73) Assignee: Sensirion AG, Stafa (CH)

( * ) Notice: Subject to any disclaimer, the term of this patent is extended or adjusted under 35 U.S.C. 154(b) by 870 days.

(21) Appl. No.: 14/311,013

(22) Filed: Jun. 20, 2014

(65) Prior Publication Data

US 2014/0377877 A1 Dec. 25, 2014

(30) Foreign Application Priority Data

Jun. 21, 2013 (EP) .................................. 13173231

(51) Int. Cl.
*G01N 33/497* (2006.01)
*G01N 33/00* (2006.01)

(52) U.S. Cl.
CPC ..... *G01N 33/4972* (2013.01); *G01N 33/0059* (2013.01); *G01N 2033/4975* (2013.01); *Y10T 436/182* (2015.01); *Y10T 436/200833* (2015.01); *Y10T 436/204165* (2015.01)

(58) Field of Classification Search
CPC ........... G01N 2033/4975; G01N 27/12; G01N 33/0059; G01N 33/497; G01N 33/4972; Y10T 436/182; Y10T 436/200833; Y10T 436/204165
See application file for complete search history.

(56) References Cited

U.S. PATENT DOCUMENTS

| | | | |
|---|---|---|---|
| 3,830,630 | A | 8/1974 | Kiefer et al. |
| 5,376,555 | A | 12/1994 | Forrester et al. |
| 5,971,937 | A | 10/1999 | Ekstroem |
| 6,858,182 | B1 | 2/2005 | Ito et al. |
| 7,919,754 | B2 | 4/2011 | Hok et al. |
| 8,280,436 | B2 | 10/2012 | Harris, Jr. |
| 2006/0237253 | A1 | 10/2006 | Mobley et al. |

(Continued)

FOREIGN PATENT DOCUMENTS

| | | |
|---|---|---|
| DE | 199 41 586 | 3/2001 |
| WO | WO 2012/097460 A1 | 7/2012 |
| WO | WO 2012/100362 A1 | 8/2012 |

OTHER PUBLICATIONS

Llobet, E. et al. "RFID Reader with gas sensing capability for monitoring fruit along the logistic chain: array development and signal processing". Proc. of SPIE vol. 6589, 2007, pp. 65890Q-1-65890Q-10.

(Continued)

*Primary Examiner* — Samuel P Siefke
(74) *Attorney, Agent, or Firm* — Foley & Lardner LLP (57) ABSTRACT

A portable electronic device comprises a chemical sensor that is sensitive to a concentration of a chemical analyte and at least two auxiliary sensors that are sensitive to parameters that are different from the concentration of the chemical analyte. The portable electronic device comprises a control device that receives signals from the chemical sensor and from the auxiliary sensors at a plurality of points in time distributed over a measurement period and correlates the time dependencies of these signals to obtain a corrected reading of the first chemical sensor. The portable electronic device may be employed for breath analysis.

13 Claims, 4 Drawing Sheets

(56) References Cited

U.S. PATENT DOCUMENTS

2010/0063409 A1    3/2010  Hoek
2012/0231841 A1    9/2012  Niederberger

OTHER PUBLICATIONS

Chaiyboun, A. et al. "Modular Analytical Multicomponent Analysis in Gas Sensor Arrays". Sensors, vol. 6, 2006, pp. 270-283.
Office Action dated Jul. 9, 2014 in related European application No. 13173231.5 (5 pgs.).
European Search Report for EP No. 13173231.5; dated Aug. 28, 2013; 6 pages.

CONCENTRATION MEASUREMENTS WITH A MOBILE DEVICE

This application claims the benefit of European Patent Application No. 13173231.5, filed on Jun. 21, 2013, the contents of which are hereby incorporated by reference in their entirety into the present disclosure.

TECHNICAL FIELD

The present invention relates to a portable electronic device comprising at least one chemical sensor, and to a method of operating a portable electronic device.

PRIOR ART

Portable electronic devices, such as mobile phones or tablet computers, are usually equipped with several sensors, e.g. a microphone, a touch screen, one or more gyroscopes, one or more acceleration sensors, a magnetic field sensor, a proximity sensor, and one or more cameras. US 2012/0231841 discloses a mobile phone equipped with a humidity sensor. WO 2012/097460 A1 suggests providing a mobile phone with a temperature sensor and a humidity sensor.

It is also possible to integrate sensors that are sensitive to one or more chemical analytes into a portable electronic device. Sensors that are sensitive to one or more chemical analytes will in the following be called "chemical sensors".

U.S. Pat. No. 8,280,436 discloses a breath analysis sensor in a mobile phone to determine a measure for the blood alcohol level of a user of the phone.

U.S. Pat. No. 5,376,555 discloses a method for determining the concentration of alveolar alcohol in a breath sample exhaled by a subject into an infrared sensing device. Mouth alcohol is detected by monitoring both alcohol and carbon dioxide with the sensing device, integrating a difference between normalized alcohol levels and carbon dioxide levels over time, and comparing the integrated difference with a threshold. Alcohol signals and carbon dioxide signals are also correlated in DE 199 41 586, U.S. Pat. No. 5,971,937 and U.S. Pat. No. 3,830,630. A correlation of an alcohol signal with carbon dioxide, humidity or temperature signals is disclosed in US 2010/0063409.

However, these disclosures fail to appropriately take into account that miniaturized sensors, in particular, miniaturized chemical sensors that are suitable to be used in portable electronic devices such as mobile phones generally have a lower accuracy and specificity than the optical sensors employed in the prior art. There is thus a need for the improvement of portable electronic devices that comprise chemical sensors. This is particularly important if the portable electronic device is to be used for breath analysis, since a user may base important decisions on the result of the breath analysis. For instance, a user may base the decision whether or not to drive a car on the result of the breath analysis, depending on the apparent blood alcohol content as determined by the breath analysis.

SUMMARY OF THE INVENTION

According to a first aspect, the present invention provides a portable electronic device comprising:
a first chemical sensor that is sensitive to a concentration of at least one first chemical analyte;
a first auxiliary sensor that is sensitive to at least one first parameter that is different from the concentration of the first chemical analyte;
at least one second auxiliary sensor that is sensitive to at least one second parameter that is different from the concentration of the first chemical analyte and different from the first parameter; and
a control device.

The control device is configured to carry out the following tasks:
receiving signals of the first chemical sensor at a plurality of points in time distributed over a measurement period,
receiving signals of the first auxiliary sensor at a plurality of points in time distributed over said measurement period,
receiving signals of the second auxiliary sensor at a plurality of points in time distributed over said measurement period, and
correlating a time dependency of the signals of the first chemical sensor, a time dependency of the signals of the first auxiliary sensor and a time dependency of the signals of the second auxiliary sensor to obtain a corrected reading of the first chemical sensor.

In other words, the transient (time-dependent) behavior of the chemical sensor and of at least two auxiliary sensors is taken into account in order to improve on the measurements taken with the chemical sensor. Of course, more than two auxiliary sensors may be employed, for instance three, four, five, six or more auxiliary sensors, and the time dependencies of their signals may be correlated with the time dependency of the signals of the first chemical sensor to obtain a corrected reading of the first chemical sensor.

The present invention is particularly useful if the first chemical sensor is a semiconductor sensor having a heated membrane, in particular, a semiconductor sensor having a heated membrane on which at least one metal oxide (MOX) layer is disposed, the conductivity of the MOX layer changing in the presence of at least one chemical analyte. Such sensors will in the following be called MOX sensors. Such sensors have often a limited specificity (i.e., they may have a cross-sensitivity to various analytes that are different from the first chemical analyte) and may have a response to the first chemical analyte that depends on environmental parameters such as humidity, temperature or mass flow. The metal oxide may be, e.g., tin oxide, tungsten oxide, gallium oxide, indium oxide, or zinc oxide. The first sensor may include a heat source integrated within the sensor. The sensor may be manufactured as described, for example, in WO 2012/100362. The first chemical sensor may be implemented on a chip, e.g. a CMOS chip. On the same chip, at least one analog-to-digital converter may be implemented to convert an analog sensor signal into a digital sensor signal. Further digital circuitry may be implemented on the same chip, such as at least one microprocessor for subjecting the digitized signal to at least one preprocessing operation, e.g., baseline correction, scaling, integration, sampling etc. Another possible measurement principle is a chemomechanical principle, in which a mass change upon absorption is transformed into a surface acoustic wave or into a cantilever resonance, for example.

Two or more of the sensors may be integrated in a single component, forming two or more sensor elements ("cells") that have different sensitivities to selected analytes or parameters. In the context of the present invention, each such sensor cell will be considered to represent a separate sensor. The sensor cells may be arranged in a one- or two-dimensional array. All or selected sensor cells may provide a sensitive layer of a material exhibiting a sensitivity to the analyte that the respective sensor cell is sensitive to.

For instance, each cell of the sensor array may specifically be mainly sensitive to a different analyte and as such may enable the portable electronic device to detect the presence or absence or concentration of such analyte. "Mainly" in this context shall mean that a sensor cell is more sensitive to the subject analyte than to other analytes. However, a sensor cell of such sensor array may exhibit not only sensitivity to its main analyte, but also a cross-sensitivity to analytes other than the main analyte. In this case, it is preferred that different sensor cells have different sensitivity profiles for the various analytes that the sensor cells are sensitive to so as to be able to separate the contributions of these analytes.

Chemical analytes to which the first chemical sensor is sensitive may include chemical elements and chemical compounds. In particular, the first chemical sensor may be sensitive to one or more of the following: alcohols such as ethanol; ketones such as acetone; aldehydes such as formaldehyde; carbon monoxide; ozone; ammonia; methane; benzene and benzene derivatives such as xylenes; thiols, in particular alkylthiols such as methyl mercaptan (methanethiol); nitric oxides (NOx). The analyte will generally be present in a fluid medium, in particular, in a gas, more particularly in air.

In a broad sense, the chemical analyte to which the first chemical sensor is sensitive may be water vapor in air, and in this sense, the term "chemical sensor" includes humidity sensors. However, in the following, the term "chemical sensor" will generally be understood to exclude humidity sensors, and a chemical sensor in a more narrow sense will be understood to be a sensor that is sensitive to at least one chemical analyte other than water. Humidity of air is accordingly understood to represent an environmental parameter, along with temperature, pressure etc.

The first and second auxiliary sensors may be any type of sensor, including, without limitation: a microphone; a light sensor (which may be color-sensitive, providing a signal substantially only for one specific wavelength range, or providing a plurality of signals for light in different wavelength regions so as to distinguish between colors); an image sensor, in particular, a camera; an inertial sensor (acceleration sensor); a gyroscope (rotation sensor); a magnetometer; a position sensor, in particular, a GPS module; a proximity sensor; a touchscreen; a joystick; a pressure sensor; a temperature sensor; a humidity sensor; a flow sensor; a thermal conductivity sensor; a specific heat sensor; a gas density sensor; a gas viscosity sensor; or another chemical sensor that has a different sensitivity to chemical analytes than the first sensor. Integration of the first and/or second auxiliary sensors on the same chip as the first chemical sensor is possible, in particular, if the first and/or second auxiliary sensors are of one of the following types: a pressure sensor; a temperature sensor; a humidity sensor; a flow sensor; a thermal conductivity sensor; a specific heat sensor; a gas density sensor; a gas viscosity sensor; or another chemical sensor.

In a preferred embodiment, at least one of the auxiliary sensors is a second chemical sensor that is sensitive to a concentration of at least one second chemical analyte that is different from the first chemical analyte. Each of the first chemical sensor and the first auxiliary sensor may be a semiconductor sensor having a heated membrane. Preferably each of the first chemical sensor and the first and second auxiliary sensors (and possible further auxiliary sensors) is a semiconductor sensor having a heated membrane. In these cases it is particularly useful to integrate the first chemical sensor and the first and/or second auxiliary sensors on a single semiconductor chip.

If the first chemical sensor has a cross-sensitivity to a second chemical analyte, the control device may be configured to correlate the time dependencies of the signals of the first chemical sensor and of the first and/or second auxiliary sensors to correct for said cross-sensitivity. A cross-sensitivity to a second chemical analyte exists if the first chemical sensor provides an output signal that depends on the concentration of the second chemical analyte. As an example, if the first chemical sensor is mainly sensitive to ethanol, but has a cross-sensitivity to an alkylthiol (a mercaptan), the first auxiliary sensor may be chosen to be a sensor that is mainly sensitive to a concentration of alkylthiols (in the following referred to as an "alkylthiol sensor"). From the time-dependent signals of the alkylthiol sensor, it is possible to measure whether and to what extent alkylthiols are present at what times during the measurement period. On the basis of these measurements, the control unit may, for instance, determine a sub-period of the measurement period during which the concentration of alkylthiols is small and use the signal of the first chemical sensor only during this time period for measuring ethanol concentration. In other embodiments, the control unit may use the time-dependent signals of the first and/or second auxiliary sensors to quantitatively correct the signal of the first chemical sensor for the contribution of another chemical analyte to which the first chemical sensor has a cross-sensitivity.

In more general terms, the first auxiliary sensor may be used to determine a sub-period of the measurement period during which the signals of the first chemical sensor are more likely to be "valid", i.e., to be representative of a parameter of interest, than during other sub-periods. Examples in the context of breath analysis, in which the parameter of interest is the concentration of an analyte in either alveolar air or upper respiratory air, are provided below.

The second auxiliary sensor may then be used for additionally limiting the sub-period during which the signals of the first chemical sensor are likely to be representative of the parameter of interest, or for other corrective purposes, including quantitative corrections. For instance, the control device may be configured to correlate the time dependencies of the signals of both the first and second auxiliary sensors to determine a sub-period of the measurement period during which the signals of the first chemical sensor are likely to be representative of the parameter of interest.

In other embodiments, the time-dependent signals of the second auxiliary sensor may be used for correction of a known dependency of the signals of the first chemical sensor to an environmental parameter to which the second auxiliary sensor is sensitive. For instance, if the second auxiliary sensor is a humidity, temperature or pressure sensor, the time-dependent signals of this sensor may be used for correction of a known humidity, temperature or pressure dependency of the signals of the first chemical sensor.

An important application is breath analysis. In breath analysis, the user's breath is analyzed for the concentration of one or more analytes that may be present in the user's breath, depending on the user's physiological condition and/or prior behavior. Breath analysis may be carried out, for instance, for determining breath alcohol content as a measure for blood alcohol content; for determining breath acetone content as an indicator of physiological activity such as "fat burning"; or for identifying undesired breath odors ("bad breath"). To this end, the first chemical sensor may be sensitive to, e.g., the concentration of ethanol, of a ketone such as acetone, or of a thiol such as an alkylthiol, in particular, methyl mercaptan. In breath analysis measurements, it may be important to distinguish between upper respiratory air ("mouth signal") and deep lung air (alveolar air, "lung signal"). For instance, when ethanol concentration is measured, only the lung signal is representative of the user's blood alcohol content, whereas the mouth signal may be strongly influenced by alcohol that has only recently been ingested. On the other hand, when the odor of the user's breath is of interest ("bad breath"), the mouth signal may be decisive. Upper respiratory air and alveolar air may be distinguished on the basis of the signals of the first and/or second auxiliary sensors. In a preferred embodiment, the first auxiliary sensor is sensitive to a concentration of carbon dioxide, as the carbon dioxide concentration is generally larger for alveolar air than for upper respiratory air. In particular, the first auxiliary sensor may be a semiconductor sensor with a heated membrane, the sensor being configured as a heat conductivity sensor. The heat conductivity of air is closely related to the air's carbon dioxide content. By monitoring the transient signals of the first auxiliary sensor, a distinction between upper respiratory air and alveolar air may be achieved.

The second auxiliary sensor is then preferably sensitive to at least one of the following environmental parameters: humidity; temperature; mass flow; noise; movements of the portable electronic device; and proximity of a user of the portable electronic device. All these parameters contribute to a determination whether and during what portions of the measurement period the portable electronic device has been handled correctly, i.e., whether and during what time the user has exhaled towards the device with sufficient strength (as measured by humidity, temperature, mass flow and/or exhalation noise), whether and during what time the user has kept the device at rest (as measured by inertial sensors and/or gyroscopes), and whether and during what time the user has kept the device sufficiently close to his/her face (as determined by a proximity sensor).

For instance, if the first chemical sensor is a sensor that is primarily sensitive to ethanol, if the first auxiliary sensor is a sensor that is sensitive to carbon dioxide concentration, and if the second auxiliary sensor is a humidity (or temperature, pressure, mass flow etc.) sensor, the first and second auxiliary sensors may be used to determine a sub-period of the measurement period during which both carbon dioxide and humidity (or temperature, pressure, mass flow etc.) are sufficiently high to indicate that it is likely that the device is receiving alveolar air.

The second auxiliary sensor may in addition be used to correct for a known humidity (or temperature, pressure, mass flow etc.) dependence of the signals of the first chemical sensor. More generally speaking, the control device may be configured to employ the time dependency of the signals of the second auxiliary sensor to correct for a cross-sensitivity of the first chemical sensor and/or of the first auxiliary sensor to the parameter to which the second auxiliary sensor is sensitive.

Examples for different possible types of second auxiliary sensors will now be discussed in more detail.

(a) For instance, if the second auxiliary sensor is a humidity sensor, the control device may be configured to determine whether and during what time during the measurement period the humidity measured by the humidity sensor indicates that the user is exhaling alveolar air in a desired manner, and to possibly correct for reduced humidity values. Relative humidity in exhaled alveolar air is normally close to 100%. In particular, the control device may be configured to monitor humidity values as a function of time. For instance, if the humidity values indicate a rise in relative humidity to a value above a certain threshold (e.g., in the range of 80%-95%) for a certain time period, this would indicate to the control device that the user is handling the portable electronic device correctly, in particular, that the user is exhaling in the correct direction, with the required intensity and for the required period of time. If no rise in humidity is detected, or if a rise is detected, but is not strong enough (e.g., if the threshold is not reached within a certain time period), or if the rise to too slow, this would indicate that the user is handling the portable electronic device incorrectly, i.e., that the user is not exhaling air in the required manner, and that therefore the first sensor might not deliver meaningful results. More complex criteria may be derived from the humidity values as a function of time. Such criteria may involve numerical integration and/or differentiation and other numerical procedures.

(b) Similarly, if the second auxiliary sensor is a temperature sensor, the control device may be configured to determine whether and during what time the temperature transient measured by the temperature sensor indicates that the user is exhaling air in a predetermined manner. The temperature of exhaled air is normally close to 37° C. Similar considerations as for a humidity sensor also apply for a temperature sensor. In particular, the control device may be configured to monitor temperature values as a function of time. For instance, if the temperature values indicate a rise in temperature to a value above a certain threshold (e.g., in the range of 33-35° C.) within a certain time period, this would indicate to the control device that the user is handling the portable electronic device correctly. If no rise in temperature is detected, or if a rise is detected, but is not strong enough (e.g., if the threshold is not reached within a certain time period), or if the rise to too slow, this would indicate that the user is handling the portable electronic device incorrectly.

(c) Similarly, if the second auxiliary sensor is a flow sensor, the control device may be configured to determine whether and during what time the flow rate measured by the flow sensor indicates that the user is exhaling air in a predetermined manner. Again, similar considerations as for a humidity or temperature sensor also apply for a flow sensor. In particular, the control device may be configured to monitor flow rate values as a function of time. For instance, if the flow rate remains above a certain threshold for a certain time period, this would indicate to the control device that the user is handling the portable electronic device correctly. If no air flow is detected, or if the detected air flow is not strong enough (e.g., if the threshold is not reached), this would indicate that the user is handling the portable electronic device incorrectly.

(d) If the second auxiliary sensor is a microphone, the control device may be configured to determine whether sound signals recorded by the microphone indicate that the user is exhaling air in a predetermined manner. Exhalation of air past a microphone will cause a particular noise pattern that may be discriminated from other noise patterns. The exact noise pattern will depend on several factors, including the type and location of the microphone in the housing of the mobile device, the geometry of the channel leading to the microphone, the flow direction of the exhaled air relative to the microphone surface, etc. If a characteristic noise pattern is detected during a certain time period, this would indicate to the control device that the user is handling the portable electronic device correctly during that time period. If no such noise pattern is detected, or if a noise pattern is detected, but is below the threshold, this would indicate that the user is handling the portable electronic device incorrectly.

(e) If the second auxiliary sensor is a proximity sensor, the control device may be configured to determine whether distance data measured by the proximity sensor indicates that the user holds the portable electronic device in a predetermined distance range from the user's face.

(f) If the second sensor is an inertial sensor or a gyroscope, the control device may be configured to determine whether measured acceleration and/or orientation of the portable electronic device indicates that the user holds the portable electronic device in a predetermined manner. For instance, if the inertial sensors and/or the gyroscope indicate rapid linear and/or rotational movements of the mobile device, or if the acceleration sensors indicate that the sensor points in an undesired direction (e.g., that the portable electronic device is oriented with its sensor facing downward), this would indicate that the user is handling the portable electronic device incorrectly.

(g) If the second sensor is an image sensor (in particular, a camera), the control device may be configured to determine whether image data recorded by the image sensor indicates that the user is holding the portable electronic device in a predetermined manner. In particular, the control device may be configured to carry out a pattern recognition algorithm to determine whether and during what time the image sensor is recording a human face. Such face recognition algorithms are well known in the art. If no human face is recorded, this would indicate that the user is handling the portable electronic device incorrectly.

In one application, the device may be configured to carry out breath analysis for breath alcohol determination. In this case the first chemical sensor may be primarily sensitive to ethanol, and the first auxiliary sensor may be sensitive to a concentration of carbon dioxide. The control device may then be configured to correlate the time dependencies of the signals of the first chemical sensor and the first auxiliary sensor to determine a sub-period of said measurement period during which the signals of the first chemical sensor represent alveolar air.

In one particular example, the first chemical sensor may be primarily sensitive to ethanol and may have a cross-sensitivity to a ketone such as acetone and/or a thiol such as an alkyl thiol, in particular, methyl mercaptan, the first auxiliary sensor may be sensitive to a concentration of carbon dioxide, and the second auxiliary sensor may be sensitive to the ketone and/or the thiol. The time dependency of the signals of the first auxiliary sensor may then be used to determine a sub-period of said measurement period during which the signals of the first chemical sensor represent alveolar air, as described above, while the time dependency of the signals of the second auxiliary sensor may be employed to correct for the cross-sensitivity of the first chemical sensor to the ketone and/or the thiol.

In another application, the portable electronic device may be configured to carry out breath analysis so as to determine the odor of a user's breath ("bad breath"). The first chemical sensor may then be sensitive to the concentration of a thiol, and the first auxiliary sensor may be sensitive to a concentration of carbon dioxide. The control device may then be configured to correlate the time dependencies of the signals of the first chemical sensor and the first auxiliary sensor to determine a sub-period of said measurement period during which the signals of the first chemical sensor represent upper respiratory breath. The time dependency of the signals of the second auxiliary sensor may be employed, e.g., to correct for a cross-sensitivity of the first chemical sensor to other analytes such as alcohols, including ethanol, and ketones, including acetone.

The portable electronic device of the present invention may be any of the following: a mobile phone, and in particular a smart phone, a handheld computer, an electronic reader, a tablet computer, a game controller, a pointing device, a photo or a video camera, a digital music player, an electronic wrist watch, a headset or a computer peripheral. This listing is to be understood as not limiting. Such portable electronic device may primarily be designed for computing and/or telecommunication and/or other tasks in the IT arena, and may be enhanced by the function of providing chemical information. The portable electronic device will generally comprise an independent energy source such as a battery to enable the portable electronic device to be operated without connecting the portable electronic device to an electricity network.

The control device of the present invention may comprise at least one microprocessor and may be configured to run a computer program element (which may be, e.g., part of an application program, of the operating system, or of a dedicated "chemical engine"). The computer program element may be stored in a memory of the portable electronic device. The control device may comprise a microprocessor implemented on the same chip as the first chemical sensor, and/or it may comprise one or more other microprocessors of the portable electronic device. The control device need not be implemented in a single piece of hardware; on the contrary, different tasks may be carried out by different hardware elements belonging to the control device.

The control device may be configured to communicate with a remote server. To this end, the portable electronic device may comprise a communication module for data exchange with the remote server (or the "cloud") through a digital communication channel. The communication module may be a wireless communication module for communication through a wireless communication channel. Often, the portable electronic device will comprise a plurality of such communication modules. Such modules may include at least one module for connecting the portable electronic device to a wireless telephony network, e.g., a GPRS module, a UMTS module, or an LTE module, or it may include a Wi-Fi module, a Bluetooth module, a near-field communication module etc. or any other module that allows the exchange of data, in particular, the exchange of data via a data network, including the Internet. The wireless communication module may comprise an antenna. The control device may then be configured to send sensor data to a remote server via the wireless communication module and to receive, in response, result data that are based on the sent sensor data. The sensor data may comprise data from the first chemical sensor, from the first auxiliary sensor and/or from the second auxiliary sensor. In other words, all or part of the algorithms for determining a corrected reading of the first chemical sensor may be carried out on a remote server ("cloud computing"). However, it is also possible that all algorithms are carried out entirely locally in the portable electronic device.

The results (e.g., the corrected reading for the first chemical sensor or any data derived therefrom) may be output by an output device, which may be, e.g., a display, a loudspeaker, a vibrator, a flash, a beamer, an LED, or a laser. More than one output device may be employed.

In another aspect, the present invention provides a method of analyzing a fluid sample with a portable electronic device comprising a first chemical sensor that is sensitive to a concentration of at least one first chemical analyte, a first auxiliary sensor that is sensitive to at least one first parameter that is different from the concentration of the first chemical analyte, and at least one second auxiliary sensor that is sensitive to at least one second parameter that is different from the concentration of the first chemical analyte and different from the first parameter. The method comprises:

receiving signals of the first chemical sensor at a plurality of points in time distributed over a measurement period;

receiving signals of the first auxiliary sensor at a plurality of points in time distributed over said measurement period;

receiving signals of the second auxiliary sensor at a plurality of points in time distributed over said measurement period; and correlating a time dependency of the signals of the chemical sensor, a time dependency of the signals of the first auxiliary sensor and a time dependency of the signals of the second auxiliary sensor to obtain a corrected reading of the first chemical sensor.

All considerations that are discussed in this document in conjunction with the portable electronic device of the present invention are equally applicable to the method of the present invention.

In particular, if the first chemical sensor has a cross-sensitivity to a second chemical analyte, the method may comprise:

correlating the time dependencies of the signals of the first chemical sensor and of the first and/or second auxiliary sensors to correct for said cross-sensitivity.

In some embodiments, the method may comprise:

correlating the time dependencies of the signals of the first chemical sensor and of the first and second auxiliary sensors to determine a sub-period of said measurement period during which the signals of the first chemical sensor represent signals that are representative of a parameter of interest.

In some embodiments, the time dependency of the signals of the second auxiliary sensor may be employed to correct for a cross-sensitivity of the first chemical sensor and/or of the first auxiliary sensor to an environmental parameter to which the second auxiliary sensor is sensitive.

The method may be employed for breath analysis. In this case the first chemical sensor may be sensitive to the concentration of ethanol, of a ketone or of a thiol, the first auxiliary sensor may be sensitive to a concentration of carbon dioxide, and the second auxiliary sensor may be sensitive to at least one of the following parameters: humidity; temperature; mass flow; noise; movements of the portable electronic device; and proximity of a user of the portable electronic device.

The method may be entirely computer-implemented. As described above, the steps of the method of the present invention may be carried out by a control device of the portable electronic device, and the control device may comprise a microprocessor. As described above, the method may involve sending sensor data to a remote server via a wireless communication module and to receive, in response, result data from said remote server via the wireless communication module, based on the sensor data sent to the remote server.

In yet another aspect, the present invention provides a computer program element comprising computer program code that, when executed in a control device of a portable electronic device, carries out the method of the present invention. The computer program element can be provided in any suitable form, including source code or object code. In particular, it can be stored on a computer-readable medium or embodied in a data stream. The data stream may be accessible through a network such as the Internet.

All considerations that are discussed in this document in conjunction with the portable electronic device and the method of the present invention are equally applicable to the computer program element of the present invention.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
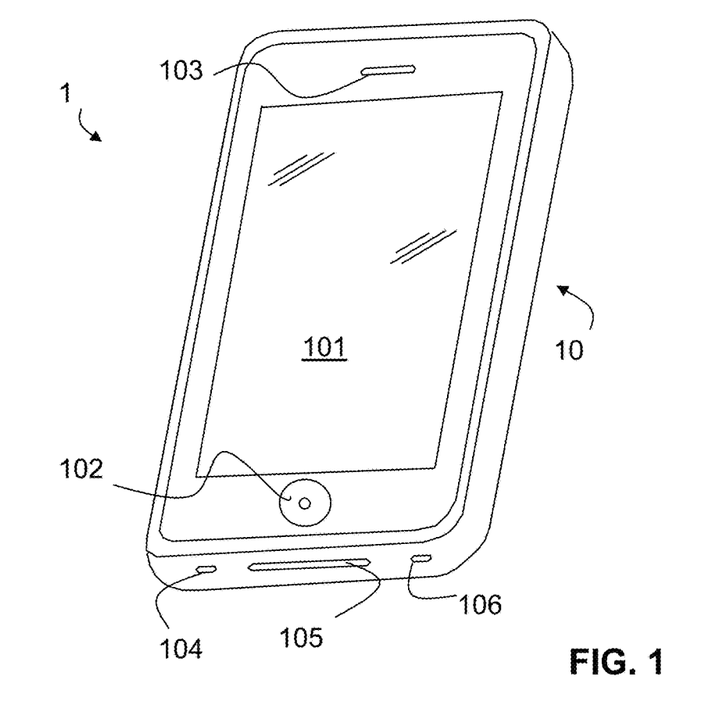
FIG. 1 is a perspective view of a portable electronic device.

FIG. 1 illustrates a portable electronic device 1 in the form of a mobile phone. The housing 10 of the mobile phone includes a front side with a touchscreen display 101, a switch button 102 and an opening 103 for a first loudspeaker. In a lower sidewall region of the housing 10, further openings 104, 105 and 106 are provided. Behind these openings, components such as a microphone, further loudspeakers and connectors are disposed. In addition, behind any of these openings sensors such as a humidity sensor, a temperature sensor and one or more sensors for detecting at least one chemical analyte (i.e., one or more chemical sensors) may be arranged.

Figure 2:
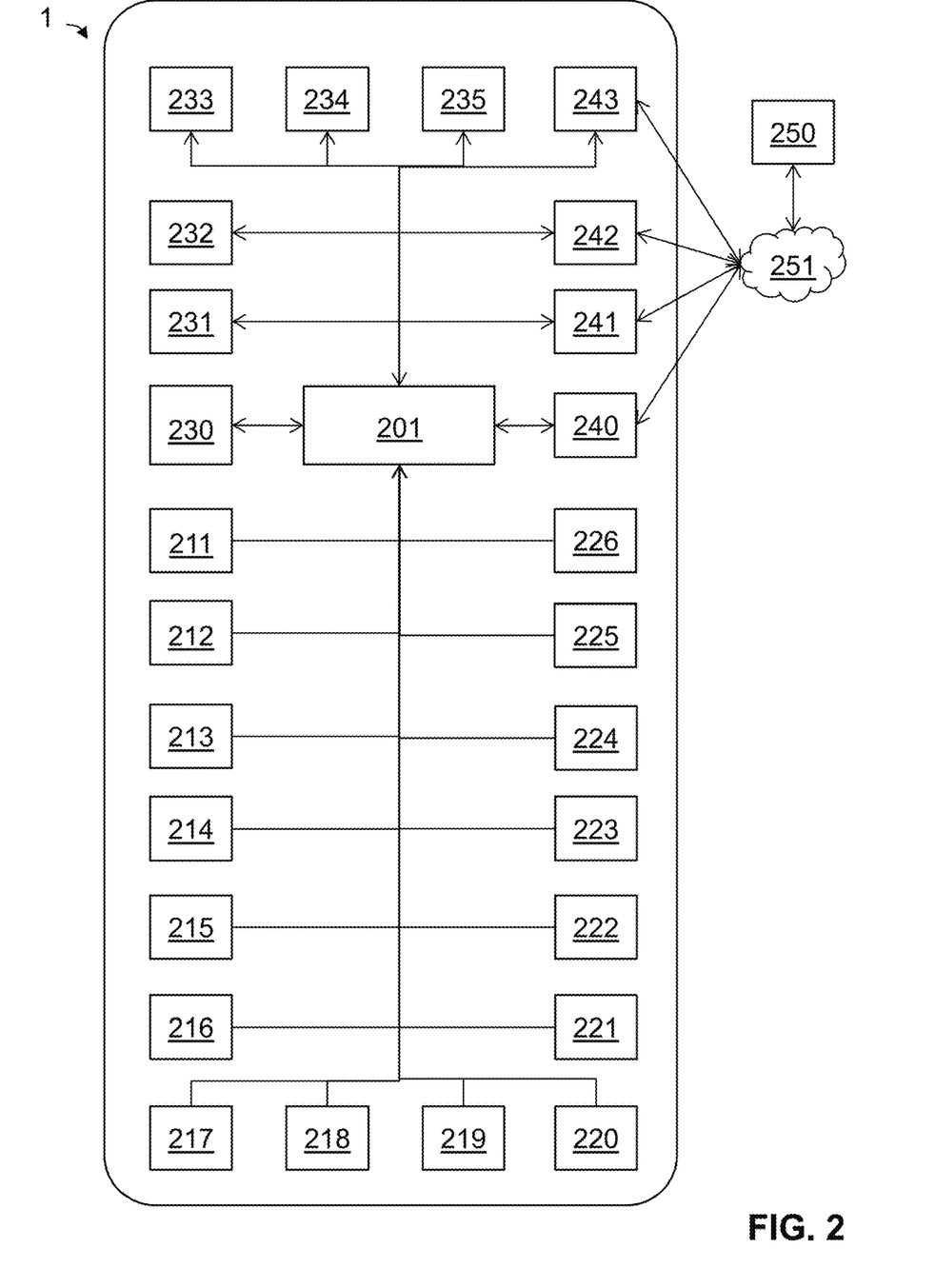
FIG. 2 is a highly schematic view illustrating the various components in a portable electronic device.

In FIG. 2, the various components that may be present in a portable electronic device are schematically illustrated. A control device 201, which will generally comprise a microprocessor and a memory, interacts with a number of input/output devices and other modules, as described in the following. Input devices may be present, e.g., as follows:

a microphone 211;
a front camera 212;
a rear camera 213;
three orthogonal inertial sensors (linear acceleration sensors) 214;
three orthogonal gyroscopes (rotation sensors) 215;
a magnetometer 216;
a GPS module 217;
a proximity sensor 218;
a light intensity sensor 219;
a pressure sensor 220;
a temperature sensor 221;
a humidity sensor 222;
a flow sensor 223;

a sensor 224 for measuring thermal conductivity of the surrounding gas; such sensor may be used for measuring $CO_2$ content in a gas;

a sensor 225 for measuring specific heat of the surrounding gas; and one ore more chemical sensors 226 that are each sensitive to at least one chemical analyte other than water.

Output devices may be present as follows:

a front loudspeaker 231 for telephony;

at least one bottom loudspeaker 232 for hands-free operation;

a vibrator 233;

a flash 234;

a status LED 235;

a Beamer 236.

Furthermore, a combined input/output device in the form of the touchscreen display 230 may be present.

Furthermore, the portable electronic device may comprise one or more wireless communication modules for exchanging data with a remote server 250 through a wireless data connection 251, such as a GPRS module 240, a UMTS module 241, a WLAN module 242 and a Bluetooth module 243. Of course, more such modules may be provided.

In the memory of the control device 201, an application program (app) and/or a routine of the operating system and/or a dedicated program ("chemical engine") may be stored for carrying out measurements with the chemical sensor 226.

Figure 3:
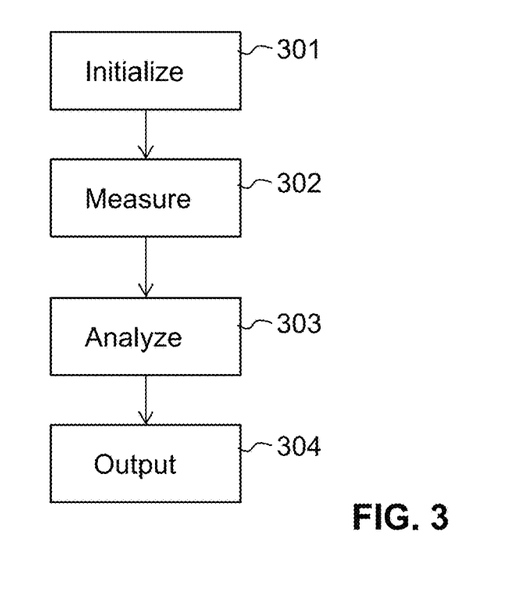
FIG. 3 is a flow diagram illustrating a method of operating the portable electronic device.

The portable electronic device may be used for various types of measurements, including breath analysis. FIG. 3 schematically illustrates a flow diagram for a typical measurement for the purpose of breath analysis.

In a first step 301, the portable electronic device is initialized. To this end, parameters needed for the measurement, such as operational parameters of the various sensors, are downloaded from a remote server (from the "cloud") or read from a memory of the portable electronic device. The chemical sensor 226 and other sensors that require heating are then heated up to their operational temperature. When the sensors are ready to take measurements, the control device 201 may cause the display 230 or the loudspeaker 232 to output a corresponding message to the user, instructing the user to begin with the measurement.

In a second step 302, a measurement operation is carried out. To this end, a plurality of sensors are operated to obtain readings from these sensors. The sensors that are operated include at least one chemical sensor that is sensitive to a particular substance of interest in the user's breath, such as ethanol, acetone or a thiol. The selected sensor(s) will in the following be collectively called the "main chemical sensor" for simplicity. The sensors that are operated further include at least two further sensors that are sensitive to other quantities, for instance, a flow sensor, a humidity sensor, a temperature sensor, a $CO_2$ sensor, a heat capacity sensor, a microphone operating as a noise level sensor, an inertial sensor, another chemical sensor that is sensitive to a different substance than the selected cell, etc. These sensors will in the following be called the "auxiliary sensors". Multiple readings are taken for the main chemical sensor and the auxiliary sensors at different points in time, so as to sample the time dependencies of all sensor signals. All sensor readings are recorded by the control device.

In a third step 303, the obtained sensor readings are analyzed by the control device. Analysis may take place entirely within the control device using algorithms stored in the portable electronic device, or the control device may send raw or pre-processed sensor data to a remote server 250 (to the "cloud") with the aid of at least one of the wireless communication modules 240-243. The remote server 250 may carry out at least part of the analysis and send result data that represent the results of the analysis back to the portable electronic device 1. The portable electronic device may then receive these data through one of the wireless communication modules 240-243. In a fourth step 304, the results of the analysis are output (e.g., displayed) to the user, and/or they are fed into another application that receives these results as an input variable.

The analysis involves a correlation of the readings of the main chemical sensor with the readings of the auxiliary sensors not only at one particular point in time, but the analysis further takes the time dependencies of these readings into account. Taking into account the time dependencies further improves the reliability and accuracy of the measurement result.

Figure 4:
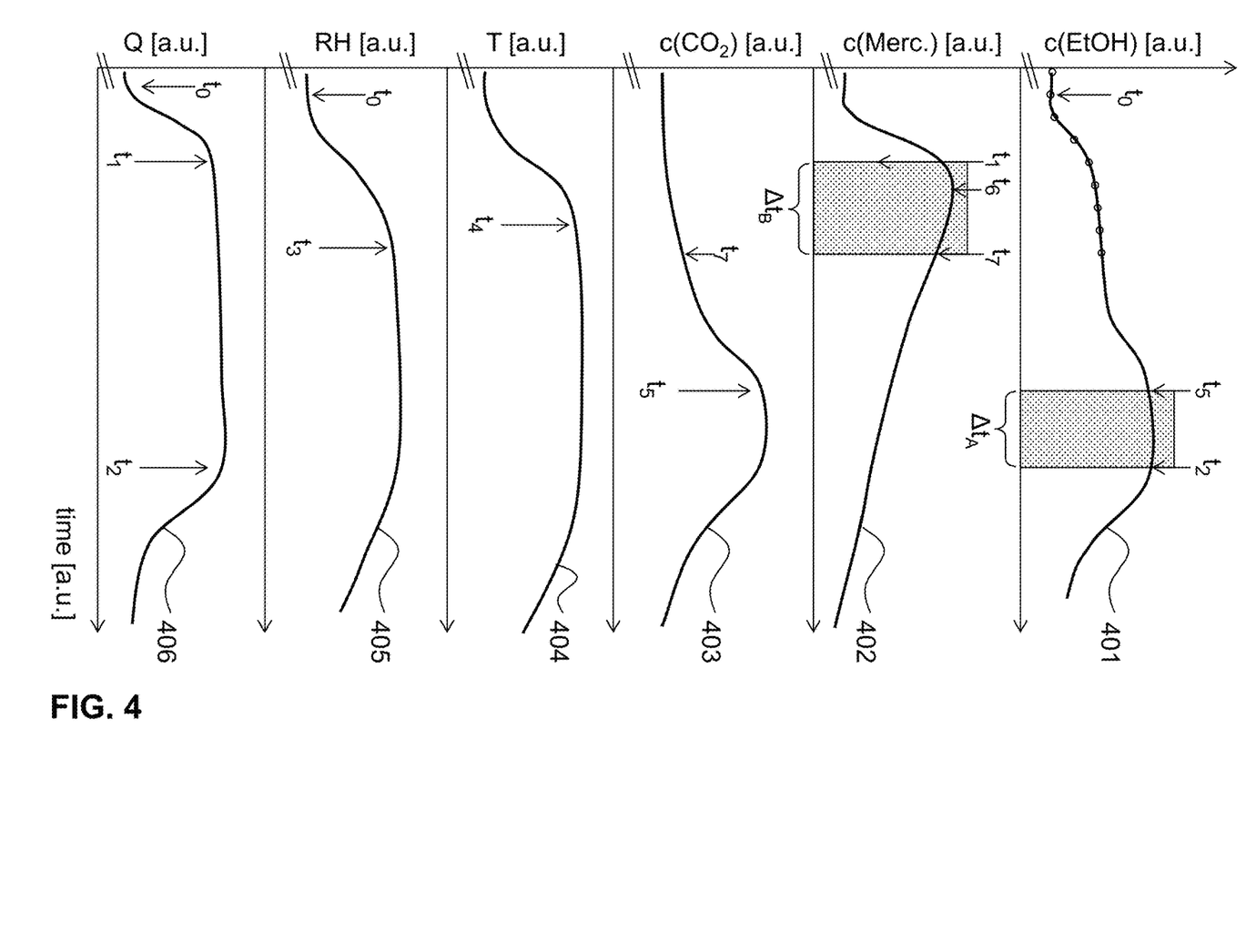
FIG. 4 is a diagram schematically illustrating the readings of different sensors in an exemplary breath analysis measurement.

A fictitious example is given with reference to FIG. 4. This Figure shows six diagrams schematically illustrating the signals of a first chemical sensor that is sensitive to ethanol (apparent ethanol concentration c(EtOH) in arbitrary units, curve 401), a second chemical sensor that is primarily sensitive to methyl mercaptan (methanethiol; methyl mercaptan concentration c(Merc.) in arbitrary units, curve 402), a carbon dioxide sensor (carbon dioxide concentration $c(CO_2)$ in arbitrary units, curve 403), a temperature sensor (apparent temperature T in arbitrary units, curve 404), a humidity sensor (apparent relative humidity RH in arbitrary units, curve 405), and a flow sensor (mass flow rate Q in arbitrary units, curve 406) during a fictitious exhalation event. These signals are sampled at regular intervals (some exemplary sampling points are indicated on curve 401).

Exhalation starts at a point in time $t_0$. Warm and humid exhaled air from the user's mouth and lungs reaches the surface of the various sensors. Initially this air will primarily originate from the mouth of the user (upper respiratory air); only later the air predominantly originates from the lungs (alveolar air). The sensors will have different response times to this stimulus. In the present example, the mass flow sensor exhibits the fastest response (curve 406), and the mass flow signal starts to rise shortly after $t_0$ and reaches a plateau at time $t_1$. The temperature sensor (curve 404) and the humidity sensor (curve 405) exhibit a slower response, thus reaching a plateau only at later times $t_3$ and $t_4$, respectively. The signals of the carbon dioxide sensor (curve 403) and of the methyl mercaptan sensor (curve 402) are governed not only by their response function, but also by the fact that carbon dioxide concentration and methyl mercaptan concentration vary between upper respiratory air from the user's mouth ("mouth signal") and alveolar air from the user's lungs ("lung signal"). Air originating from the user's lungs will generally have a much higher carbon dioxide concentration than air from the user's mouth. This leads to a delayed response of the carbon dioxide sensor to exhalation of the user, the carbon dioxide signal exceeding an initial threshold of, e.g., 1 vol-% at a time $t_7$ and reaching a plateau only at a time $t_5$. On the other hand, air originating from the user's mouth will often have higher mercaptan content ("bad breath") than air from the lungs, due to the presence of mercaptan-producing bacteria in the oral cavity. Therefore the mercaptan signal may have a peak at already a time $t_6$, well before the plateau of the carbon dioxide signal. The signal of the ethanol sensor (curve 401) will be influenced by air both from the mouth and from the lungs, albeit to different extents. Normally the lung signal will be much stronger than the mouth signal; however, if the user has consumed an alcoholic beverage shortly before the measurement, the mouth signal can be stronger.

Only the lung signal is representative of the blood alcohol content of the user. It is therefore desirable to distinguish between the mouth signal and the lung signal. This can be achieved by correlating the time dependencies of several sensors. In the present example, the carbon dioxide signal (curve 403), the mercaptan signal (curve 402) and the flow signal (curve 406) can be used to determine a time period during which the ethanol signal best represents the lung signal. For instance, the processing algorithm may determine that a lung signal is present only if the following criteria are cumulatively fulfilled: (a) The mass flow signal is above a certain threshold and has reached a plateau; (b) the carbon dioxide signal is above a certain threshold and has reached a plateau; (c) the mercaptan signal has already exceeded a peak value and decreases again, or the mercaptan signal has remained below a certain threshold during the entire exhalation event; and (d) the ethanol signal has reached a plateau. In the present example, these criteria are fulfilled during the time interval $\Delta t_A$, lasting from $t_5$ (the time at which the $CO_2$ signal has reached a plateau) to $t_2$ (the time when the mass flow signal starts to decrease). This time interval can be taken as the best estimate for the presence of the lung signal, and the readings of the ethanol sensor are further processed only for this time period.

It should be noted that the criterion whether or not a measured variable f(t) has reached a plateau requires an analysis of the time dependency of the variable. For instance, one might define that a plateau has been reached if the (discretized and possibly time-averaged) first time derivative df(t)/dt, i.e., the gradient, has been positive and is now in a certain narrow band around zero, and if the (discretized and possibly time-averaged) second time derivative $d^2f(t)/d^2t$, i.e., the curvature, has first been positive, has then crossed zero, has then been negative and has approached zero again. Of course, other definitions are possible, but all such definitions will involve a determination of the time dependency of the variable. The same is true if it is to be determined whether or not a variable has reached a peak.

It is of course possible to take more parameters into account. For instance, further parameters may be the intensity of a typical breathing noise, as determined by a microphone of the portable electronic device, indicating that the user has actually blown into the portable electronic device; the magnitude of the output of a proximity sensor indicating that the user has held the portable electronic device close to a body part, etc.

The determination of such parameters not only enables a distinction between the mouth signal and the lung signal, but also the detection of attempts to "cheat" the device. For instance, if the user uses a fan in order to create mass flow instead of blowing at the device, a different time dependence of the $CO_2$ signal will result.

Furthermore, the readings of the various sensors may be employed to correct the ethanol reading during the time interval of interest. For instance, the $CO_2$ concentration in alveolar air is known to be typically between 4 and 5 vol-%, the relative humidity is known to be close to 100%, and the temperature is known to be close to 37° C. If the other sensors indicate a significantly lower $CO_2$ concentration, a significantly lower humidity and/or a significantly lower temperature, this may indicate dilution of the exhaled air by surrounding air, and the reading of the ethanol sensor may be corrected accordingly. Likewise, if the signal of the ethanol sensor is known to have a certain humidity dependency, this humidity dependency can be compensated on the basis of the signal of the humidity sensor. If the ethanol sensor is known to have a cross-sensitivity to methyl mercaptan, this can be compensated on the basis of the signal of the mercaptan sensor.

In the previous example, all criteria were applied in a binary fashion. In particular, the time interval that is representative for the lung signal was determined on the basis of whether or not several criteria are fulfilled, in an on/off fashion. In more complex implementations, a time-dependent "lung signal indicator" may be calculated from the time dependencies of the various measured parameters, and the measured ethanol signal may be weighted to a different extent depending on the value of the "lung signal indicator".

If, on the other hand, it is desired to determine "bad breath", the main interest may be in the mouth signal, and it will again be desirable to distinguish between the mouth signal and the lung signal. This can be done in a similar manner as described above in conjunction with the ethanol measurements. For instance, the processing algorithm may determine that a mouth signal is present only if the following criteria are cumulatively fulfilled: (a) The mass flow signal is above a certain threshold and has reached a plateau; (b) the carbon dioxide signal is below a certain threshold; and (c) the mercaptan signal is close to a peak value. It is of course possible to define more such criteria. In the present example, these criteria are fulfilled during the time interval $\Delta t_B$, lasting from $t_1$ to $t_7$. This time interval can be taken as the best estimate for the presence of the mouth signal, and the readings of the mercaptan sensor are further processed only for this time period.

In a similar manner, other kinds of breath analysis measurements can be carried out, e.g., measurements of acetone concentration in a user's breath.

Figure 5:
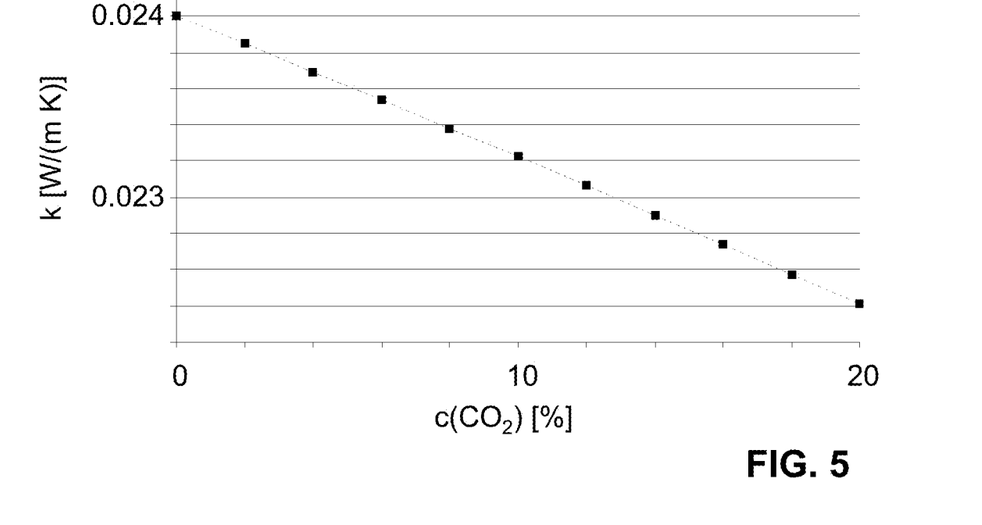
FIG. 5 is a diagram illustrating the correlation between carbon dioxide concentration $c(CO_2)$ and thermal conductivity k.

FIG. 5 illustrates the manner in which the concentration $c(CO_2)$ of carbon dioxide in air can be determined by measuring the thermal conductivity k. The thermal conductivity k decreases essentially linearly with increasing $CO_2$ concentration in the depicted range of 0-20 mol-%. By measuring the thermal conductivity k, the $CO_2$ concentration in air can be accurately determined. Thermal conductivity sensors exist in a variety of forms, including semiconductor-based thermal conductivity sensors. Such sensors may employ a membrane that is heated at constant power. The temperature of the membrane will then depend on the thermal conductivity of the surrounding gas. Alternatively, the membrane may be heated to a constant temperature, and the heating power may be determined. Reaction times of such sensors can be well below 2 seconds, making them suitable for the type of measurements discussed here.

Figure 6:
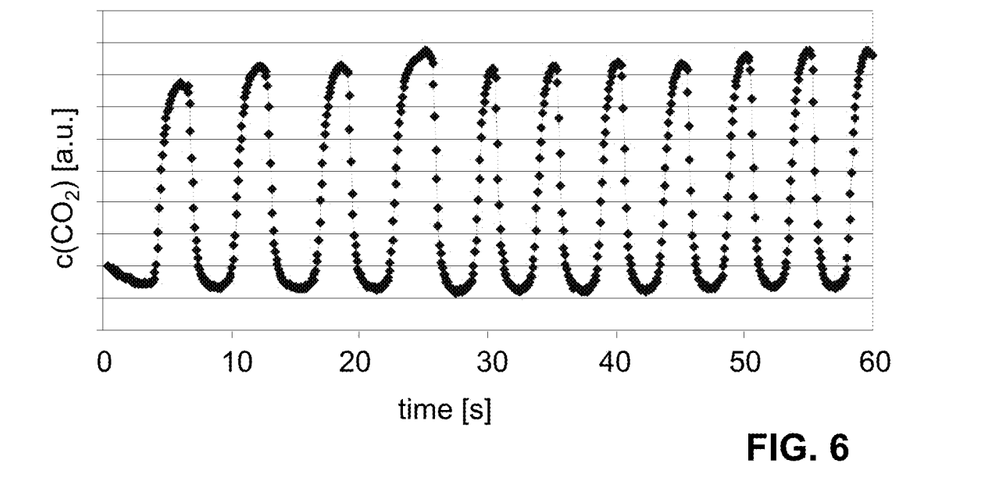
FIG. 6 is a diagram illustrating the measured variation in carbon dioxide concentration (on an arbitrary scale, not taking into account offsets) over time during several breathing cycles of a human, as determined by thermal conductivity measurements.

FIG. 6 illustrates the response of a carbon dioxide sensor to several human breath cycles. A male person (65 kg, 22 years) inhaled and exhaled through an enclosed space in which the sensor was disposed while breathing normally. The sensor signal was recorded for 60 seconds. The carbon dioxide sensor was based on thermal conductivity measurements as described in conjunction with FIG. 5. The figure illustrates that a response signal with high signal-to-noise ratio can be obtained, leading to measurements with a high degree of reliability and reproducibility.

The invention claimed is:
1. A portable electronic device comprising:
   a first chemical sensor that is sensitive to a concentration of at least one of a first chemical element and a first chemical compound, the first chemical sensor being a semiconductor sensor having a heated membrane, the first chemical sensor having a cross-sensitivity to at least one of a second chemical element and a second chemical compound;
a first auxiliary sensor that is sensitive to at least one first parameter that is different from the concentration of the at least one the first chemical element and the first chemical compound;
at least one second auxiliary sensor that is sensitive to at least one second parameter that is different from the concentration of the at least one the first chemical element and the first chemical compound and different from the first parameter; and
a control device configured to carry out the following steps:
receiving signals of the first chemical sensor at a plurality of points in time distributed over a measurement period;
receiving signals of the first auxiliary sensor at a plurality of points in time distributed over said measurement period;
receiving signals of the second auxiliary sensor at a plurality of points in time distributed over said measurement period;
correlating a time dependency of the signals or the first chemical sensor, a time dependency of the signals of the first auxiliary sensor and a time dependency of the signals of the second auxiliary sensor to determine a sub-period of the measurement period during which the signals of the first chemical sensor represent signals that are representative of a parameter of interest, and wherein the sub-period is determined such that at least one of a value of the first parameter and a value of the second parameter is above or below a threshold during the sub-period; and
determining a corrected reading of the first chemical sensor corresponding to the sub-period,
wherein the correlation of the time dependencies of the signals of the first chemical sensor and at least one of the first and second auxiliary sensors is carried out to correct for said cross-sensitivity.

2. A method of analyzing a fluid sample with a portable electronic device comprising a first chemical sensor that is sensitive to a concentration of at least one of a first chemical element and a first chemical compound, the first chemical sensor being a semiconductor sensor having a heated membrane, the first chemical sensor having a cross-sensitivity to at least one of a second chemical element and a second chemical compound, a first auxiliary sensor that is sensitive to at least one first parameter that is different from the concentration of the at least one of the first chemical element and the first chemical compound, and at least one second auxiliary sensor that is sensitive to at least one second parameter that is different from the concentration of the at least one of the first chemical element and the first chemical compound and different from the first parameter, the method comprising:
receiving signals of the first chemical sensor at a plurality of points in time distributed over a measurement period;
receiving signals of the first auxiliary sensor at a plurality of points in time distributed over said measurement period;
receiving signals of the second auxiliary sensor at a plurality of points in time distributed over said measurement period;
correlating a time dependency of the signals of the first chemical sensor, a time dependency of the signals of the first auxiliary sensor and a time dependency of the signals of the second auxiliary sensor to determine a sub-period of said measurement period during which the signals of the first chemical sensor represent signals that are representative of a parameter of interest, and wherein the sub-period is determined such that at least one of a value of the first parameter and a value of the second parameter is above or below a threshold during the sub-period; and
determining a corrected reading of the first chemical sensor corresponding to the sub-period, wherein the time dependencies of the signals of the first chemical sensor and at least one of the first and second auxiliary sensors are correlated to correct for said cross-sensitivity.

3. The method of claim 2, wherein the method is a method for breath analysis, wherein the first chemical sensor is sensitive to the concentration of ethanol, of a ketone or of a thiol, wherein the first auxiliary sensor is sensitive to a concentration of carbon dioxide, and wherein the second auxiliary sensor is sensitive to at least one of the following parameters:
humidity;
temperature;
mass flow;
noise;
movements of the portable electronic device; and
proximity of a user of the portable electronic device.

4. The method of claim 2, wherein the signals of the first chemical sensor, the signals of the first auxiliary sensor, and the signals of the second auxiliary sensor are correlated at more than one particular point in time.

5. The method according to claim 2, wherein determining the corrected reading of the first chemical sensor corresponding to the sub-period comprises determining the corrected reading of the first chemical sensor based on a subset of the signals of the first chemical sensor that omits at least some of the signals of the first chemical sensor that were detected outside of the sub-period.

6. A computer program element containing computer program code that causes a portable electronic device comprising a first chemical sensor that is sensitive to a concentration of at least one of a first chemical element and a first chemical compound, the first chemical sensor being a semiconductor sensor having a heated membrane, the first chemical sensor having a cross-sensitivity to at least one of a second chemical element and a second chemical compound, a first auxiliary sensor that is sensitive to at least one first parameter that is different from the concentration of the at least one of the First chemical element and the first chemical compound, at least one second auxiliary sensor that is sensitive to at least one second parameter that is different from the concentration of the at least one of the first chemical element and the first chemical compound and different from the first parameter, and a control device programmed to carry out the following method:
receiving signals of the first chemical sensor at a plurality of points in time distributed over a measurement period;
receiving signals of the first auxiliary sensor at a plurality of points in time distributed over said measurement period;
receiving signals of the second auxiliary sensor at a plurality of points in time distributed over said measurement period;
correlating a time dependency of the signals of the first chemical sensor, a time dependency of the signals of the first auxiliary sensor and a time dependency of the signals of the second auxiliary sensor to determine a sub-period of the measurement period during which the signals of the first chemical sensor represent signals that are representative of a parameter of interest, and wherein the sub-period is determined such that at least one of a value of the first parameter and a value of the second parameter is above or below a threshold during the sub-period; and determining a corrected reading of the first chemical sensor corresponding to the sub-period, wherein the time dependencies of the signals of the first chemical sensor and at least one of the first and second auxiliary sensors are correlated to correct for said cross-sensitivity.

7. The portable electronic device of claim 1, wherein the control device is configured to employ the time dependency of the signals of the second auxiliary sensor to correct for a cross-sensitivity of at least one of the first chemical sensor and of the first auxiliary sensor to an environmental parameter to which the second auxiliary sensor is sensitive.

8. The portable electronic device of claim 1, wherein the portable electronic device is configured to carry out breath analysis, wherein the first chemical sensor is sensitive to the concentration of ethanol, of a ketone or of a thiol, wherein the first auxiliary sensor is sensitive to a concentration of carbon dioxide, and wherein the second auxiliary sensor is sensitive to at least one of the following parameters:
humidity;
temperature;
mass flow;
noise;
movements of the portable electronic device; and
proximity of a user of the portable electronic device.

9. The portable electronic device of claim 1, wherein the portable electronic device is configured to carry out breath analysis so as to measure the presence of ethanol in a user's breath, wherein the first chemical sensor is sensitive to a concentration of ethanol, wherein the first auxiliary sensor is sensitive to a concentration of carbon dioxide, and wherein the control device is configured to correlate the time dependencies of the signals of the first chemical sensor and the first auxiliary sensor to determine a sub-period of said measurement period during which the signals of the first chemical sensor represent alveolar air.

10. The portable electronic device of claim 1, wherein the portable electronic device is configured to carry out breath analysis so as to determine breath odor in a user's breath, wherein the first chemical sensor is sensitive to the concentration of a thiol, wherein the first auxiliary sensor is sensitive to a concentration of carbon dioxide, and wherein the control device is configured to correlate the time dependencies of the signals of the first chemical sensor and the first auxiliary sensor to determine a sub-period of said measurement period during which the signals of the first chemical sensor represent upper respiratory air.

11. The portable electronic device of claim 1, wherein the first auxiliary sensor is a second chemical sensor that is sensitive to a concentration of at least one of the second chemical element and the second chemical compound that is different from the at least one of the first chemical element and the first chemical compound, and wherein each of the first chemical sensor and the first auxiliary sensor is a semiconductor sensor having a heated membrane.

12. The portable electronic device of claim 1, wherein the control device is configured to employ the time dependency of the signals of the second auxiliary sensor to correct for a cross-sensitivity of at least one of the first chemical sensor and of the first auxiliary sensor to an environmental parameter to which the second auxiliary sensor is sensitive.

13. The method of claim 1, wherein the time dependency of the signals of the second auxiliary sensor is employed to correct for a cross-sensitivity of at least one of the first chemical sensor and of the first auxiliary sensor to an environmental parameter to which the second auxiliary sensor is sensitive.

* * * * *